United States Patent [19]

Wang et al.

[11] Patent Number: 5,116,738
[45] Date of Patent: May 26, 1992

[54] DNA SEQUENCES ENCODING

[75] Inventors: Elizabeth A. Wang, Carlisle; John M. Wozney, Hudson; Vicki Rosen, Brookline, all of Mass.

[73] Assignee: Genetics Institute, Inc., Cambridge, Mass.

[21] Appl. No.: 692,827

[22] Filed: Apr. 26, 1991

Related U.S. Application Data

[63] Continuation of Ser. No. 179,197, Apr. 8, 1988, abandoned, which is a continuation-in-part of Ser. No. 28,285, Mar. 20, 1987, abandoned, and Ser. No. 943,332, Dec. 17, 1986, abandoned, and Ser. No. 880,776, Jul. 1, 1986, abandoned.

[30] Foreign Application Priority Data

Jun. 30, 1987 [US] United States .. PCT/US87/01537

[51] Int. Cl.⁵ .................. C12P 21/02; C12P 19/34; C12N 15/00; C12N 7/00; C12N 5/00; C12N 1/16; C12N 1/18; C12N 15/70; C12N 15/85; C07H 15/12; C07K 3/00

[52] U.S. Cl. .................. 435/69.1; 435/91; 435/172.3; 435/235.1; 435/320.1; 435/252.3; 435/252.33; 435/240.2; 435/255; 435/256; 536/27; 530/350

[58] Field of Search .......... 435/69.1, 91, 172.3, 435/235.1, 320.1, 252.3, 252.33, 240.1, 240.2, 255, 256; 536/27; 530/350; 935/18, 31, 32, 58, 62, 70, 72, 73

[56] References Cited

U.S. PATENT DOCUMENTS

| | | | |
|---|---|---|---|
| 4,294,753 | 10/1981 | Urist | 530/395 |
| 4,434,094 | 2/1984 | Seyedin et al. | 530/416 |
| 4,563,350 | 1/1986 | Nathan | 424/95 |
| 4,608,199 | 8/1986 | Caplan et al. | 530/414 |
| 4,619,989 | 10/1986 | Urist | 530/417 |
| 4,627,982 | 12/1986 | Seyedin et al. | 424/95 |
| 4,681,763 | 7/1987 | Nathanson | 424/95 |
| 4,737,578 | 4/1988 | Evans | 530/350 |
| 4,761,471 | 8/1988 | Urist | 530/350 |
| 4,774,228 | 9/1988 | Seyedin | 514/21 |
| 4,774,322 | 9/1988 | Seyedin | 530/353 |
| 4,789,732 | 12/1988 | Urist | 530/350 |
| 4,795,804 | 1/1989 | Urist | 530/350 |
| 4,798,885 | 1/1989 | Mason | 530/350 |
| 4,804,744 | 2/1989 | Sen | 530/350 |
| 4,810,691 | 3/1989 | Seyedin | 514/2 |
| 4,843,063 | 6/1989 | Seyedin | 514/2 |
| 4,968,590 | 11/1990 | Kuberasampath et al. | 530/326 |
| 5,011,691 | 4/1991 | Oppermann | 424/423 |

FOREIGN PATENT DOCUMENTS

| | | |
|---|---|---|
| 2017466 | 2/1990 | Canada . |
| 336760 | 6/1989 | European Pat. Off. . |
| 409472A1 | 1/1991 | European Pat. Off. . |
| 416578A2 | 3/1991 | European Pat. Off. . |
| WO89/09787 | 10/1989 | World Int. Prop. O. . |
| WO89/09788 | 10/1989 | World Int. Prop. O. . |
| WO90/03733 | 4/1990 | World Int. Prop. O. . |
| WO91/02744 | 3/1991 | World Int. Prop. O. . |
| WO91/05802 | 5/1991 | World Int. Prop. O. . |

OTHER PUBLICATIONS

Mariahs, T., Molecular Cloning, A Laboratory Manual Cold Spring Harbor Laboratory, CJH, N.Y. (1982).

Seggs, S. V. et al., Proc. Natl. Acad. Sci. USA, vol. 78 pp. 6613-6617 (1981).

Urist et al., Science 220: 680-686 (1983).

Luyten et al., The Journal of Biological Chemistry 264(23): 13377-13380 (Aug. 15, 1989).

Sampath, et al., Proc. Natl. Acad. Sci. 84: 7109-7113 (1987).

Primary Examiner—Joan Ellis
Attorney, Agent, or Firm—Ellen J. Kapinos; Bruce M. Eisen

[57] ABSTRACT

Purified BMP-3 proteins and processes for producing them are disclosed. They may be used in the treatment of bone and cartilage defects and in wound healing and related tissue repair.

18 Claims, 5 Drawing Sheets

FIGURE 1A

```
        383        393        403        413   (1)                  428
GAGGAGGAAG CGGTCTACGG GGGTCCTTCT GCCTCTGCAG  AAC AAT GAG CTT CCT GGG GCA
                                             Asn Asn Glu Leu Pro Gly Ala 443                458                473              488
GAA TAT CAG TAC AAG GAG GAT GAA GTA TGG GAG GAG AGG AAG CCT TAC AAG ACT
Glu Tyr Gln Tyr Lys Glu Asp Glu Val Trp Glu Glu Arg Lys Pro Tyr Lys Thr 503                518                533
CTT CAG ACT CAG CCC CCT GAT AAG AGT AAG AAC AAA AAG AAA CAG AGG AAG GGA
Leu Gln Thr Gln Pro Pro Asp Lys Ser Lys Asn Lys Lys Lys Gln Arg Lys Gly 548              563                578                593
CCT CAG CAG AAG AGT CAG ACG CTC CAG TTT GAT GAA CAG ACC CTG AAG AAG GCA
Pro Gln Gln Lys Ser Gln Thr Leu Gln Phe Asp Glu Gln Thr Leu Lys Lys Ala 608                623                638
AGA AGA AAG CAA TGG ATT GAA CCC CGG AAT TGT GCC AGA CGG TAC CTT AAA GTG
Arg Arg Lys Gln Trp Ile Glu Pro Arg Asn Cys Ala Arg Arg Tyr Leu Lys Val 653              668                683                698
GAC TTC GCA GAT ATT GGC TGG AGC GAA TGG ATT ATT TCC CCC AAG TCC TTC GAT
Asp Phe Ala Asp Ile Gly Trp Ser Glu Trp Ile Ile Ser Pro Lys Ser Phe Asp 713                728              743 (111)         756
GCC TAT TAC TGC TCC GGA GCG TGC CAG TTC CCC ATG CCA AAG  GTAGCCATTG
Ala Tyr Tyr Cys Ser Gly Ala Cys Gln Phe Pro MET Pro Lys 766        776        786
TTTTTTGTCC TGTCCTTCCC ATTTCCATAG
```

FIGURE 1B

```
    284        294        304    (112)            319
CTAACCTGTG TTCTCCCTTT TCGTTCCTAG TCT TTG AAG CCA TCA AAT CAC GCT ACC
                                 Ser Leu Lys Pro Ser Asn His Ala Thr 334                349                364                379
ATC CAG AGT ATA GTG AGA GCT GTG GGG GTC GTC CCT GGA ATC CCC GAG CCT TGC
Ile Gln Ser Ile Val Arg Ala Val Gly Val Val Pro Gly Ile Pro Glu Pro Cys 394                409                424                439
TGT GTG CCA GAA AAG ATG TCC TCA CTC AGC ATC TTA TTC TTT GAT GAA AAC AAG
Cys Val Pro Glu Lys MET Ser Ser Leu Ser Ile Leu Phe Phe Asp Glu Asn Lys 454                469                484         (175)
AAT GTG GTA CTT AAA GTA TAT CCA AAC ATG ACA GTA GAG TCT TGT GCT TGC AGA
Asn Val Val Leu Lys Val Tyr Pro Asn MET Thr Val Glu Ser Cys Ala Cys Arg 503       513       523       533
TAACCTGGTG AAGAACTCAT CTGGATGCTT AACTCAATCG
```

FIGURE 2

```
        10         20         30         40         50         60         70
AGATCTTGAA AACACCCGGG CCACACACGC CGCGACCTAC AGCTCTTTCT CAGCGTTGGA GTGGAGACGG 80         90        100        110        120        130        140
CGCCCGCAGC GCCCTGCGCG GGTGAGGTCC GCGCAGCTGC TGGGGAAGAG CCCACCTGTC AGGCTGCGCT 150        160        170        180        190        200        210
GGGTCAGCGC AGCAAGTGGG GCTGGCCGCT ATCTCGCTGC ACCCGGCCGC GTCCGGGCT CCGTGCGCCC 220        230        240        250        260        270        280
TCGCCCCAGC TGGTTTGGAG TTCAACCCTC GGCTCCGCCG CCGGCTCCTT GCGCCTTCGG AGTGTCCCGC 290        300        310        320 (1)               335
AGCGACGCCG GGAGCCGACG CGCCGCGCGG GTACCTAGCC ATG GCT GGG GCG AGC AGG CTG CTC
                                             MET Ala Gly Ala Ser Arg Leu Leu
```

```
       350                365                380                395
TTT CTG TGG CTG GGC TGC TTC TGC GTG AGC CTG GCG CAG GGA GAG AGA CCG AAG CCA
Phe Leu Trp Leu Gly Cys Phe Cys Val Ser Leu Ala Gln Gly Glu Arg Pro Lys Pro 410                425                440                455
CCT TTC CCG GAG CTC CGC AAA GCT GTG CCA GGT GAC CGC ACG GCA GGT GGT GGC CCG
Pro Phe Pro Glu Leu Arg Lys Ala Val Pro Gly Asp Arg Thr Ala Gly Gly Gly Pro 470                485                500                515
GAC TCC GAG CTG CAG CCG CAA GAC AAG GTC TCT GAA CAC ATG CTG CGG CTC TAT GAC
Asp Ser Glu Leu Gln Pro Gln Asp Lys Val Ser Glu His MET Leu Arg Leu Tyr Asp 530                545                560
AGG TAC AGC ACG GTC CAG GCG GCC CGG ACA CCG GGC TCC CTG GAG GGA GGC TCG CAG
Arg Tyr Ser Thr Val Gln Ala Ala Arg Thr Pro Gly Ser Leu Glu Gly Gly Ser Gln 575                590                605                620
CCC TGG CGC CCT CGG CTC CTG CGC GAA GGC AAC ACG GTT CGC AGC TTT CGG GCG GCA
Pro Trp Arg Pro Arg Leu Leu Arg Glu Gly Asn Thr Val Arg Ser Phe Arg Ala Ala 635                650                665                680
GCA GCA GAA ACT CTT GAA AGA AAA GGA CTG TAT ATC TTC AAT CTG ACA TCG CTA ACC
Ala Ala Glu Thr Leu Glu Arg Lys Gly Leu Tyr Ile Phe Asn Leu Thr Ser Leu Thr 695                710                725                740
AAG TCT GAA AAC ATT TTG TCT GCC ACA CTG TAT TTC TGT ATT GGA GAG CTA GGA AAC
Lys Ser Glu Asn Ile Leu Ser Ala Thr Leu Tyr Phe Cys Ile Gly Glu Leu Gly Asn
```

FIGURE 2 (CONTINUED)

```
          755                     770                     785                    800
ATC AGC CTG AGT TGT CCA GTG TCT GGA GGA TGC TCC CAT CAT GCT CAG AGG AAA CAC
Ile Ser Leu Ser Cys Pro Val Ser Gly Gly Cys Ser His His Ala Gln Arg Lys His 815                     830                     845
ATT CAG ATT GAT CTT TCT GCA TGG ACC CTC AAA TTC AGC AGA AAC CAA AGT CAA CTC
Ile Gln Ile Asp Leu Ser Ala Trp Thr Leu Lys Phe Ser Arg Asn Gln Ser Gln Leu 860                     875                     890                     905
CTT GGC CAT CTG TCA GTG GAT ATG GCC AAA TCT CAT CGA GAT ATT ATG TCC TGG CTG
Leu Gly His Leu Ser Val Asp MET Ala Lys Ser His Arg Asp Ile MET Ser Trp Leu 920                     935                     950                    965
TCT AAA GAT ATC ACT CAA TTC TTG AGG AAG GCC AAA GAA AAT GAA GAG TTC CTC ATA
Ser Lys Asp Ile Thr Gln Phe Leu Arg Lys Ala Lys Glu Asn Glu Glu Phe Leu Ile 980                     995                    1010                   1025
GGA TTT AAC ATT ACG TCC AAG GGA CGC CAG CTG CCA AAG AGG AGG TTA CCT TTT CCA
Gly Phe Asn Ile Thr Ser Lys Gly Arg Gln Leu Pro Lys Arg Arg Leu Pro Phe Pro 1040                    1055                    1070                   1085
GAG CCT TAT ATC TTG GTA TAT GCC AAT GAT GCC GCC ATT TCT GAG CCA GAA AGT GTG
Glu Pro Tyr Ile Leu Val Tyr Ala Asn Asp Ala Ala Ile Ser Glu Pro Glu Ser Val 1100                    1115                    1130
GTA TCA AGC TTA CAG GGA CAC CGG AAT TTT CCC ACT GGA ACT GTT CCC AAA TGG GAT
Val Ser Ser Leu Gln Gly His Arg Asn Phe Pro Thr Gly Thr Val Pro Lys Trp Asp 1145                    1160                    1175                    1190
AGC CAC ATC AGA GCT GCC CTT TCC ATT GAG CGG AGG AAG AAG CGC TCT ACT GGG GTC
Ser His Ile Arg Ala Ala Leu Ser Ile Glu Arg Arg Lys Lys Arg Ser Thr Gly Val 1205                    1220                    1235                   1250
TTG CTG CCT CTG CAG AAC AAC GAG CTT CCT GGG GCA GAA TAC CAG TAT AAA AAG GAT
Leu Leu Pro Leu Gln Asn Asn Glu Leu Pro Gly Ala Glu Tyr Gln Tyr Lys Lys Asp 1265                    1280                    1295                   1310
GAG GTG TGG GAG GAG AGA AAG CCT TAC AAG ACC CTT CAG GCT CAG GCC CCT GAA AAG
Glu Val Trp Glu Glu Arg Lys Pro Tyr Lys Thr Leu Gln Ala Gln Ala Pro Glu Lys 1325                    1340                    1355                   1370
AGT AAG AAT AAA AAG AAA CAG AGA AAG GGG CCT CAT CGG AAG AGC CAG ACG CTC CAA
Ser Lys Asn Lys Lys Lys Gln Arg Lys Gly Pro His Arg Lys Ser Gln Thr Leu Gln 1385                    1400                    1415
TTT GAT GAG CAG ACC CTG AAA AAG GCA AGG AGA AAG CAG TGG ATT GAA CCT CGG AAT
Phe Asp Glu Gln Thr Leu Lys Lys Ala Arg Arg Lys Gln Trp Ile Glu Pro Arg Asn
```

FIGURE 2 (CONTINUED)

```
     1430              1445     (377)    1460                   1475
TGC GCC AGG AGA TAC CTC AAG GTA GAC TTT GCA GAT ATT GGC TGG AGT GAA TGG ATT
Cys Ala Arg Arg Tyr Leu Lys Val Asp Phe Ala Asp Ile Gly Trp Ser Glu Trp Ile 1490              1505              1520                   1535
ATC TCC CCC AAG TCC TTT GAT GCC TAT TAT TGC TCT GGA GCA TGC CAG TTC CCC ATG
Ile Ser Pro Lys Ser Phe Asp Ala Tyr Tyr Cys Ser Gly Ala Cys Gln Phe Pro MET 1550              1565              1580                   1595
CCA AAG TCT TTG AAG CCA TCA AAT CAT GCT ACC ATC CAG AGT ATA GTG AGA GCT GTG
Pro Lys Ser Leu Lys Pro Ser Asn His Ala Thr Ile Gln Ser Ile Val Arg Ala Val 1610              1625              1640                   1655
GGG GTC GTT CCT GGG ATT CCT GAG CCT TGC TGT GTA CCA GAA AAG ATG TCC TCA CTC
Gly Val Val Pro Gly Ile Pro Glu Pro Cys Cys Val Pro Glu Lys MET Ser Ser Leu 1670              1685              1700
AGT ATT TTA TTC TTT GAT GAA AAT AAG AAT GTA GTG CTT AAA GTA TAC CCT AAC ATG
Ser Ile Leu Phe Phe Asp Glu Asn Lys Asn Val Val Leu Lys Val Tyr Pro Asn MET 1715              1730     (472)    1746         1756         1766         1776
ACA GTA GAG TCT TGC GCT TGC AGA TAACCTGGCA AAGAACTCAT TTGAATGCTT AATTCAATCT
Thr Val Glu Ser Cys Ala Cys Arg

1786
CTAGAGTCGA CGGAATTC
```

DNA SEQUENCES ENCODING

This application is a continuation of U.S. Ser. No. 179,197 filed Apr. 8, 1988 now abandoned which is a continuation-in-part of U.S. Ser. Nos. 028,285 filed Mar. 20, 1987; 943,332 filed Dec. 17, 1986; and 880,776 filed Jul. 1, 1986; all now abandoned. This application also claims priority of PCT/US887/01537 filed Jun. 30, 1987.

The present invention relates to a novel family of purified proteins designated BMP-3 proteins and processes for obtaining them. These proteins may be used to induce bone and/or cartilage formation and in wound healing and tissue repair.

BMP-3 proteins are produced by culturing a cell transformed with a cDNA substantially as shown in Table II and recovering from the culture medium a protein containing substantially the 96 amino acid sequence as shown in Table II from amino acid #377 through amino acid #472.

Some members of the BMP-3 protein family are further characterized by the ability of 200 nanograms of the BMP-3 protein to score at least +2 in the Rosen-modified Sampath-Reddi assay of bond and/or cartilage formation described in Example III.

Another aspect of the invention provides pharmaceutical compositions containing a therapeutically effective amount of a BMP-3 protein in admixture with a pharmaceutically acceptable vehicle or carrier. The compositions may be used for bone and/or cartilage formation BMP-3 compositions may also be used for wound healing and tissue repair. Compositions of the invention may further include other therapeutically useful agents such as the BMP proteins BMP-1, BMP-2A, and BMP-2B disclosed respectively in co-owned and concurrently filed pending U.S. patent applications Ser. No. 179,101 and Ser. No. 179,100. Other therapeutically useful agents include growth factors such as epidermal growth factor (EGF), fibroblast growth factor (FGF), and transforming growth factor (TGF). The compositions may also include an appropriate matrix, for instance, for supporting the compositions and providing a surface for bone and/or cartilage growth. The compositions may be employed in methods for treating a number of bone defects and periodontal disease and various types of wounds. These methods, according to the invention, entail administering to a patient needing such bone and-/or cartilage formation, wound healing, or tissue repair an effective amount of a novel BMP-3 protein of the present invention. These methods may also entail the administration of a BMP-3 protein of the invention in conjunction with at least one of the novel BMP proteins disclosed in co-owned applications described above. In addition, these methods may also include administration of BMP-3 with other growth factors.

Still a further aspect of the invention are DNA sequences coding on expression for a BMP-3 protein. Such sequences include the sequence of nucleotides in a 5' to 3' direction illustrated in Tables I A and I B and II or DNA sequences which hybridize under stringent conditions with the DNA sequences of Tables I A and I B and II and encode a protein having the ability of 200 nanograms of the protein to score at least +2 in the Rosen-modified Sampath-Reddi assay of bone and/or cartilage formation described in Example III. Finally, allelic or other variations of the sequences of Tables I A and I B and II, whether such nucleotide changes result in changes in the peptide sequence or not, are also included in the present invention.

Still a further aspect of the invention is a vector containing a DNA sequence as described above in operative association with an expression control sequence therefor. Such vector may be employed in a novel process for producing a BMP-3 protein of the invention in which a cell line transformed with a DNA sequence encoding expression of a BMP-3 protein in operative association with an expression control sequence therefor, is cultured in a suitable culture medium and a BMP-3 protein is isolated and purified therefrom. This claimed process may employ a number of known cells both prokaryotic and eukaryotic as host cells for expression of the polypeptide.

Other aspects and advantages of the present invention will be apparent upon consideration of the following detailed description and preferred embodiments thereof.

BRIEF DESCRIPTION OF THE DRAWINGS

FIGS. 1A and 1B comprise partial DNA sequence and derived amino acid sequence of bovine BMP-3 from bacteriophage lambda bP-819 ATCC #40344. FIGS. 1A and 1B correspond to Tables IA and IB further described below.

FIG. 2 comprises DNA sequence and derived amino acid sequence of human BMP-3 from lambda H128-4 ATCC #40437. FIG. 2 corresponds to Table II further described below.

DETAILED DESCRIPTION OF THE INVENTION

The purified BMP-3 proteins of the present invention are produced by culturing a host cell transformed with a cDNA sequence substantially as shown in Table II and recovered from the culture medium. The recovered BMP-3 proteins are characterized by the 96 amino acid sequence of a substantially homologous sequence as amino acid #377 to amino acid #472 as shown in Table II. Some BMP-3 proteins are also characterized by the ability of 200 nanograms (ng) of the protein to score at least +2 in the Rosen-modified Sampath-Reddi assay of bond and/or cartilage formation described in Example III.

The BMP-3 proteins provided herein also include proteins encoded by the sequences similar to those of Tables I A and I B and II, but into which modifications are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of Tables I A and I B and II. These sequences, by virtue of sharing primary, secondary, or tertiary structural and conformational characteristics with BMP-3 proteins of Tables I A and I B and II may possess biological properties in common therewith. Thus, they may be employed as biologically active substitutes for naturally-occurring BMP-3 polypeptides in therapeutic processes.

Other specific mutations of the sequences of BMP-3 described herein involve modifications of one or both of the glycosylation sites. The absence of glycosylation or only partial glycosylation results from amino acid substitution or deletion at one or both of the asparagine-linked glycosylation recognition sites present in the sequences of the BMP-3 shown in Tables I A and I B and II. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence.

The present invention also encompasses the novel DNA sequences, free of association with DNA sequences encoding other proteinaceous materials, and coding on expression for a BMP-3 protein. These DNA sequences include those depicted in Tables I A and I B and II in a 5' to 3' direction and those sequences which hybridize under stringent hybridization conditions [see, T. Maniatis et al, *Molecular Cloning (A Laboratory Manual)*, Cold Spring Harbor Laboratory (1982), pages 387 to 389] to the DNA sequences of Tables I A and I B and II.

Similarly, DNA sequences which code for a BMP-3 polypeptides coded for by the sequences of Tables I A and I B and II, but which differ in codon sequence due to the degeneracies of the genetic code or allelic variations (naturally-occurring base changes in the species population which may or may not result in an amino acid change) also encode the novel growth factors described herein. Variations in the DNA sequences of Tables I A and I B and II which are caused by point mutations or by induced modifications (including insertion, deletion, and substitution) to enhance the activity, half-life or production of the polypeptides encoded thereby are also encompassed in the invention.

Another aspect of the present invention provides a novel method for producing BMP-3 proteins. The method of the present invention involves culturing a suitable cell or cell line, which has been transformed with a DNA sequence coding on expression for a BMP-3 polypeptide of the invention, under the control of known regulatory sequences. Suitable cells or cell lines may be mammalian cells, such as Chinese hamster ovary cells (CHO). The selection of suitable mammalian host cells and methods for transformation, culture, amplification, screening and product production and purification are known in the art. See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446. Another suitable mammalian cell line, which is described in the accompanying examples, is the monkey COS-1 cell line. The mammalian cell line CV-1 may also be useful.

Bacterial cells may also be suitable hosts. For example, the various strains of *E. coli* (e.g., HB101, MC1061) are well-known as host cells in the field of biotechnology. Various strains of *B. subtilis*, Pseudomonas, other bacilli and the like may also be employed in this method.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

Another aspect of the present invention provides vectors for use in the method of expression of these novel BMP-3 polypeptides. Preferably the vectors contain the full novel DNA sequences described above which code for the novel BMP-3 factors of the invention. Additionally the vectors also contain appropriate expression control sequences permitting expression of the BMP-3 protein sequences Alternatively, vectors incorporating modified sequences as described above are also embodiments of the present invention and useful in the production of the BMP-3 proteins. The vectors may be employed in the method of transforming cell lines and contain selected regulatory sequences in operative association with the DNA coding sequences of the invention which are capable of directing the replication and expression thereof in selected host cells. Useful regulatory sequences for such vectors are known to one of skill in the art and may be selected depending upon the selected host cells. Such selection is routine and does not form part of the present invention.

A protein of the present invention, which induces cartilage and/or bone growth in circumstances where bone is not normally formed, has application in the healing of bone fractures and cartilage defects in humans and other animals. Such a preparation employing a BMP-3 protein may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A BMP-3 protein of the invention may be valuable in the treatment of periodontal disease, and in other tooth repair processes. Such agents may provide an environment to attract bone-forming cells, stimulate growth of bone-forming cells or induce differentiation of progenitors of bone-forming cells. A variety of osteogenic, cartilage-inducing and bond inducing factors have been described. See, e.g. European patent applications 148,155 and 169,016 for discussions thereof.

The proteins of the invention may also be used in wound healing and tissue repair in humans and other animals. The types of wounds include, but are not limited to burns, incisions, and ulcers. (See, e.g., PCT Publication WO84/01106 for discussion of wound healing and related tissue repair). Of course, the proteins of the invention may have other therapeutic uses.

A further aspect of the invention is a therapeutic method and composition for repairing fractures and other conditions related to cartilage and/or bone defects or periodontal diseases. In addition, the invention comprises therapeutic methods and compositions for wound healing and tissue repair. Such compositions comprise a therapeutically effective amount of a BMP-3 protein in admixture with a pharmaceutically acceptable vehicle, carrier or matrix. It is expected that BMP-3 may act in concert with or perhaps synergistically with other related proteins and growth factors. Further therapeutic methods and compositions of the invention therefore comprise a therapeutic amount of a BMP-3 with a therapeutic amount of at least one of the other BMP proteins disclosed in co-owned and concurrently filed applications as described above. Further, a BMP-3 protein of the invention may be combined with other agents beneficial to the treatment of the cartilage and/or bone defect, wound or tissue in question. These agents include various growth factors such as epidermal growth factor (EGF), platelet derived growth factor (PCGF), transforming growth factor (TGF), insulinlike growth factor (IGF) and fibroblast growth factor (FGF). The preparation and formulation of such physiologically acceptable protein compositions, having due regard to pH, isotonicity, stability and the like, is within the skill of the art. The therapeutic compositions of the invention are also presently valuable for veterinary applications due to the lack of species specificity in BMP proteins. Particularly domestic animals and thoroughbred horses in addition to humans are desired patients for such treatment with BMP-3 proteins.

The therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and related tissue repair. Preferably, for bone and/or cartilage formation, the bone growth inductive factor composition would include a matrix capable of delivering the bone inductive factor to the site of bone and/or cartialge damage, providing a surface and support structure for the developing bone and cartilage and optimally capable of being resorbed into the body. Such matrices may be formed of materials presently in use for other implanted medical applications.

The choice of matrix material is based on, for example, biocompatibility, biodegradability, mechanical properties, cosmetic appearance and interface properties. The particular application of the BMP-3 compositions will determine the appropriate formulation. Potential matrices for the compositions may be biodegradable and chemically defined such as calcium sulfate, tricalciumphosphate, hydroxyapatite, polylactic acid, and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may also be altered in composition, such as in calcium-aluminate-phosphate and processing to alter for example, pore size, particle size, particle shape, and biodegradability.

The dosage regimen will be determined by the attending physician considering various factors which modify the action of the BMP-3 protein, e.g. amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the types of BMP proteins in the composition. The addition of other known growth factors, such as IGF I (insulin like growth factor I), to the final composition, may also effect the dosage.

Generally, the dosage regimen for cartialge and/or bone formation should be in the range of approximately 10 to $10^6$ nanograms of protein per gram of bone weight desired. Progress can be monitored by periodic assessment of bone growth and/or repair, e.g. x-rays.

The following examples illustrate practice of the present invention in recovering and characterizing a bovine BMP-3 protein and employing them to recover a human BMP-3 protein, obtaining a human BMP-3 protein and in expressing BMP-3 proteins via recombinant techniques.

EXAMPLE I

Isolation of Bovine Bone Inductive Factor

Ground bovine bone powder (20-120 mesh, Helitrex) is prepared according to the procedures of M. R. Urist et al., *Proc. Natl Acad. Sci USA*, 70:3511 (1973) with elimination of some extraction steps as identified below. Ten kgs of the ground powder is demineralized in successive changes of 0.6N HCl at 4° C. over a 48 hour period with vigorous stirring. The resulting suspension is extracted for 16 hours at 4° C. with 50 liters of 2M $CaCl_2$ and 10 mM ethylenediamine-tetraacetic acid [EDTA], and followed by extraction for 4 hours in 50 liters of 0.5M EDTA. The residue is washed three times with distilled water before its resuspension in 20 liters of 4M guanidine hydrochloride [GuCl], 20 mM Tris (pH 7.4), 1 mM N-ethylmaleimide, 1 mM iodoacetamide, 1 mM phenylmethylsulfonyl fluorine as described in *Clin. Orthop. Rel. Res.*, 171: 213 (1982). After 16 to 20 hours the supernatant is removed and replaced with another 10 liters of GuCl buffer. The residue is extracted for another 24 hours.

The crude GuCl extracts are combined, concentrated approximately 20 times on a Pellicon apparatus with a 10,000 molecular weight cut-off membrane, and then dialyzed in 50 mM Tris, 0.1M NaCl, 6M urea (pH7.2), the starting buffer for the first column. After extensive dialysis the protein is loaded on a 4 liter DEAE cellulose column and the unbound fractions are collected.

The unbound fractions are concentrated and dialyzed against 50 mM NaAc, 50 mM NaCl (pH 4.6) in 6M urea. The unbound fractions are applied to a carboxymethyl cellulose column. Protein not bound to the column is removed by extensive washing with starting buffer, and the material containing protein having bone and/or cartilage formation activity as measured by the Rosen-modified Sampath-Reddi rat bone formation assay (described in Example III below) is desorbed from the column by 50 mM NaAc, 0.25 mM NaCl, 6M urea (pH 4.6). The protein from this step elution is concentrated 20- to 40- fold, then diluted 5 times with 80 mM $KPO_4$, 6M urea (pH6.0). The pH of the solution is adjusted to 6.0 with 500 mM $K_2HPO_4$. The sample is applied to an hydroxylapatite column (LKB) equilibrated in 80 mM $KPO_4$, 6M urea (pH6.0) and all unbound protein is removed by washing the column with the same buffer. Protein having bone and/or cartilage formation activity as measured by the rat bone formation assay is eluted with 100 mM $KPO_4$ (pH7.4) and 6M urea.

The protein is concentrated approximately 10 times, and solid NaCl added to a final concentration of 0.15M. This material is applied to a heparin - Sepharose column equilibrated in 50 mM $KPO_4$, 150 mM NaCl, 6M urea (pH7.4). After extensive washing of the column with starting buffer, a protein with bone and/or cartilage formation activity is eluted by 50 mM $KPO_4$, 700 mM NaCl, 6M urea (pH7.4). This fraction is concentrated to a minimum volume, and 0.4 ml aliquots are applied to Superose 6 and Superose 12 columns connected in series, equilibrated with 4M GuCl, 20 mM Tris (pH7.2) and the columns developed at a flow rate of 0.25 ml/min. The protein demonstrating bone and/or cartilage inductive activity has a relative migration on SDS-PAGE corresponding to an approximately 28,000 to 30,000 dalton protein.

The above fractions from the superose columns are pooled, dialyzed against 50 mM NaAc, 6M urea (pH4.6), and applied to a Pharmacia MonoS HR column. The column is developed with a gradient to 1.0M NaCl, 50 mM NaAc, 6M urea (pH4.6). Active fractions are pooled and brought to pH3.0 with 10% trifluoroacetic acid (TFA). The material is applied to a 0.46×25 cm Vydac C4 column in 0.1% TFA and the column developed with a gradient to 90% acetonitrile, 0.1% TFA (31.5% acetonitrile, 0.1% TFA to 49.5% acetonitrile, 0.1% TFA in 60 minutes at 1 ml per minute). Active bone and/or cartilage forming material is eluted at approximately 40-44% acetonitrile. Aliquots of the appropriate active fractions are iodinated by one of the following methods: P. J. McConahey et al, *Int. Arch. Allergy.* 29:185-189 (1966); A. E. Bolton et al, *Biochem J.*, 133:529 (1973); and D. F. Bowen-Pope, *J. Biol. Chem.*, 237:5161 (1982). The iodinated proteins present in these fractions are analyzed by SDS gel electrophoresis and urea Triton ×100 isoelectric focusing. At this stage, the bone inductive factor is estimated to be approximately 10-50% pure.

EXAMPLE II

Characterization of Bovine Bone Inductive Factor

A. Molecular Weight

Approximately 20 ug protein from Example I is lyophilized and redissolved in 1X SDS sample buffer. After 15 minutes of heating at 37° C., the sample is applied to a 15% SDS polyacrylamide gel and then electrophoresed with cooling. The molecular weight is determined relative to prestained molecular weight standards (Bethesda Research Labs). Immediately after completion, the gel lane containing the bone and/or cartilage forming material is sliced into 0.3 cm pieces. Each piece is mashed and 1.4 ml of 0.1% SDS is added. The samples are shaken gently overnight at room temperature to elute the protein. Each gel slice is desalted to prevent interference in the biological assay. The supernatant from each sample is acidified to pH 3.0 with 10% TFA, filtered through a 0.45 micron membrane and loaded on a 0.46 cm×5 cm C4 Vydac column developed with a gradient of 0.1% TFA to 0.1% TFA, 90% CH$_3$CN. The appropriate bone and/or cartilage inductive protein-containing fractions are pooled and reconstituted with 20 mg rat matrix and assayed. In this gel system, the majority of bone and/or cartilage formation fractions have the mobility of a protein having a molecular weight of approximately 28,000-30,000 daltons.

B. Isoelectric Focusing

The isoelectric point of the protein having bone and/or cartilage formation activity is determined in a denaturing isoelectric focusing system. The Triton X100 urea gel system (Hoeffer Scientific) is modified as follows: 1) 40% of the ampholytes used are Servalyte 3/10; 60% are Servalyte 7-9; and 2) the catholyte used is 40 mM NaOH. Approximately 20 ug of protein from Example I is lyophilized, dissolved in sample buffer and applied to the isoelectrofocusing gel. The gel is run at 20 watts, 10° C. for approximately 3 hours. At completion the lane containing bone and/or cartilage inductive factor is sliced into 0.5 cm slices. Each piece is mashed in 1.0 ml 6M urea, 5 mM Tris (pH 7.8) and the samples agitated at room temperature. The samples are acidified, filtered, desalted and assayed as described above. The major portion of activity as determined by the Rosen-modified Sampath-Reddi assay migrates in a manner consistent with a pI of about 8.8-9.2.

C. Subunit Characterization

The subunit composition of the isolated bovine bone protein is also determined. Pure bone inductive factor is isolated from a preparative 15% SDS gel as described above. A portion of the sample is then reduced with 5 mM DTT in sample buffer and re-electrophoresed on a 15% SDS gel. The approximately 28-30 kd protein yields two major bands at approximately 18-20 kd and approximately 16-18 kd, as well as a minor band at approximately 28-30 kd. The broadness of the two bands indicates heterogeneity caused most probably by glycosylation, other post translational modification, proteolytic degradation or carbamylation.

EXAMPLE III

Rosen Modified Sampath-Reddi Assay

A modified version of the rat bone formation assay described in Sampath and Reddi, *Proc. Natl. Acad. Sci. U.S.A.*, 80:6591-6595 (1983) is used to evaluate bone and/or cartilage activity of the bovine protein obtained in Example I and the BMP-1 proteins of the invention. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then redissolved in 0.1% TFA, and the resulting solution added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21-49 day old male Long Evans rats. The implants are removed after 7-14 days. Half of each implant is used for alkaline phosphatase analysis [See, A. H. Reddi et al., *Proc. Natl Acad Sci.*, 69:1601 (1972)].

The other half of each implant is fixed and processed for histological analysis. About 1 um glycolmethacrylate sections are stained with Von Kossa and acid fuschin to score the amount of induced bone and cartilage formation present in each implant. The terms +1 through +5 represent the area of each histological section of an implant occupied by new bone and/or cartilage cells and matrix. A score of +5 indicates that greater than 50% of the implant is new bone and/or cartilage produced as a direct result of protein in the implant. A score of +4, +3, +2 and +1 would indicate that greater than 40%, 30%, 20% and 10% respectively of the implant contains new cartilage and/or bone.

The rat matrix samples containing at least 200 ng of protein obtained in Example I result in bone and/or cartilage formation that filled more than 20% of the implant areas that was sectioned for histology. This protein therefore scores at least +2 in the Rosen-modified Sampath-Reddi assay. The dose response of the matrix samples indicates that the amount of bone and/or cartilage formed increases with the amount of protein in the sample. The control sample did not result in any bone and/or cartilage formation. The purity of the protein assayed is approximately 10-15% pure.

The bone and/or cartilage formed is physically confined to the space occupied by the matrix. Samples are also analyzed by SDS gel electrophoresis and isoelectric focusing as described above, followed by autoradiography. Analysis reveals a correlation of activity with protein bands at 28-30 kd and a pI of approximately 8.8-9.2. To estimate the purity of the protein in a particular fraction an extinction coefficient of 1 OD/mg-cm is used as an estimate for protein and the protein is run on SDS PAGE followed by silver straining or radioiodination and autoradiography.

EXAMPLE IV

Bovine BMP-3

The protein composition of Example IIA of molecular weight 28-30 kd is reduced as described in Example IIC and digested with trypsin. Eight tryptic fragments are isolated by standard procedures having the following amino acid sequences:

| Fragment 1: | A | A | F | L | G | D | I | A | L | D | E | E | D | L | G |
|---|---|---|---|---|---|---|---|---|---|---|---|---|---|---|---|
| Fragment 2: | A | F | Q | V | Q | Q | A | A | D | L | | | | | |
| Fragment 3: | N | Y | Q | D | M | V | V | E | G | | | | | | |
| Fragment 4: | S | T | P | A | Q | D | V | S | R | | | | | | |
| Fragment 5: | N | Q | E | A | L | R | | | | | | | | | |
| Fragment 6: | L | S | E | P | D | P | S | H | T | L | E | E | | | |
| Fragment 7: | F | D | A | Y | Y | | | | | | | | | | |
| Fragment 8: | L | K | P | S | N | ? | A | T | I | Q | S | ] | V | E | |

A less highly purified preparation of protein from bovine bone is prepared according to a purification scheme similar to that described in Example I. The purification basically varies from that previously described by omission of the DE-52 column, the CM cellulose column and the mono S column, as well as a reversal in the order of the hydroxylapatite and heparin sepharose columns. Briefly, the concentrated crude 4M extract is brought to 85% final concentration of ethanol at 4 degrees. The mixture is then centrifuged, and the precipitate redissolved in 50 mM Tris, 0.15 M NaCl, 6.0 M urea. This material is then fractionated on Heparin Sepharose as described. The Heparin bound material is fractionated on hydroxyapatite as described. The active fractions are pooled, concentrated, and fractionated on a high resolution gel filtration (TSK 30000 in 6M guanidinium chloride, 50 mM Tris, pH 7.2). The active fractions are pooled, dialyzed against 0.1% TFA, and then fractionated on a C4 Vydac reverse phase column as described. The preparation is reduced and electrophoresed on an acrylamide gel. The protein corresponding to the 16-18kd band is eluted and digested with trypsin. Tryptic fragments are isolated having the following amino acid sequences:

| Fragment 9: | S | L | K | P | S | N | H | A | T | I | Q | S | ? | V |
|---|---|---|---|---|---|---|---|---|---|---|---|---|---|---|
| Fragment 10: | S | F | D | A | Y | Y | C | S | ? | A | | | | |
| Fragment 11: | V | Y | P | N | M | T | V | E | S | C | A | | | |
| Fragment 12: | V | D | F | A | D | I | ? | W | | | | | | |

Tryptic Fragments 7 and 8 are noted to be substantially the same as Fragments 10 and 9, respectively.

Probes consisting of pools of oligonucleotides (or unique oligonucleotides) are designed on the basis of the amino acid sequences of the tryptic Fragments 9 (Probe #3), 10 (Probe #2), and 11 (Probe #1), according to the method of R. Lathe, *J. Mol. Biol.*, 183(1): 1-12 (1985), and synthesized on an automated DNA synthesizer; the probes are then radioactively labeled with polynucleotide Kinase and $^{32}$P-ATP.

| Probe #1: | A | C | N | G | T | C | A | T | [A/G] | T | T | N | G | G | [A/G] | T | A |
|---|---|---|---|---|---|---|---|---|---|---|---|---|---|---|---|---|---|
| Probe #2: | C | A | [A/G] | T | A | [A/G] | T | A | N | G | C | [A/G] | T | C | [A/G] | A | A |
| Probe #3: | T | G | [A/G/T] | A | T | N | G | T | N | G | C | [A/G] | T | G | [A/G] | T | T |

Because the genetic code is degenerate (more than one codon can code for the same amino acid), the number of oligonucleotides in a probe pool is reduced based on the frequency of codon usage in eukaryotes, the relative stability of G:T base pairs, and the relative infrequency of the dinucleotide CpG in eukaryotic coding sequences [See Toole et al., *Nature*, 312:342-347 (1984)].

A recombinant bovine genomic library is constructed as follows: Bovine liver DNA is partially digested with the restriction endonuclease enzyme Sau 3A and sedimented through a sucrose gradient. Size fractionated DNA in the range of 15-30kb is then ligated to the bacteriophage Bam HI vector EMBL3[Frischauf et al, J. Mol. Biol., 170:827-842 (1983)]. The library is plated at 8000 recombinants per plate. Duplicate nitrocellulose replicas of the plaques are made and amplified according to a modification of the procedure of Woo et al, Proc. Natl. Acad. Sci. USA, 75:3688-91 (1978). 400,000 recombinants are screened in duplicate with Probe #1 which has been labeled with $^{32}$P. The probes are hybridized in 3M tetramethylammonium chloride (TMAC), 0.1M sodium phosphate pH6.5, 1mM EDTA, 5X Denhardts, 0.6% SDS, 100ug/ml salmon sperm DNA at 48 degrees C, and washed in 3M TMAC, 50 mM Tris pH8.0 at 50 degrees C. These conditions minimize the detection of mismatches to the 17 mer probe pool [see, Wood et al, Proc. Natl. Acad. Sci, U.S.A., 82:1585-1588 (1985)]. All recombinants which hybridized to this probe are replated for secondaries. Triplicate nitrocellulose replicas are made of the secondary plates, and amplified as described. The three sets of filters are hybridized to Probes #1, #2 and #3, again under TMAC conditions. One clone, lambda bP-819, hybridizes to all three probes and is plaque purified and DNA is isolated from a plate lysate. Bacteriophage lambda bP-819 was deposited with the American Type Culture Collection, 12301 Parklawn Drive, Rockland, Md. USA (hereinafter the ATCC) on Jun. 16, 1987 under accession number 40344. This deposit as well as the other deposits contained herein meets the requirements of the Budapest Treaty on the International Recognition of the Deposit of Microorganisms for the Purposes of Patent Procedure and Regulations thereunder. This bP-819 clone encodes at least a portion of the bovine protein which we have designated BMP-3 or bBMP-3.

The region of bP-819 which hybridizes to Probe #2 is localized and sequenced. The partial DNA and derived amino acid sequences of this region are shown in Table IIA. The amino acid sequences corresponding to tryptic Fragments 10 and 12 are underlined. The first underlined sequence corresponds to Fragment 12 while the second corresponds to Fragment 10. This region of bP-819, therefore, which hybridizes to Probe #2 encodes at least 111 amino acids. This amino acid sequence is encoded by the DNA sequence from nucleotide #414 through #746 sponding to tryptic Fragments 9 and 11 are underlined. The first underlined sequence corresponds to Fragment 9 while the second underlined sequence corresponds to Fragment 11. The peptide sequence of this region of bP-819 which hybridizes to Probe #1 and #3 is 64 amino acids in length encoded by nucleotide #305 through #493 of Table IIB. The arginine residue encoded by the AGA triplet is presumed to be the carboxy-terminus of the protein based on the presence of a stop codon (TAA) adjacent to it. The nucleic acid sequence preceding the couplet TC (positions 305-306) is presumed to be an intron (non-coding sequence) based on the presence of a consensus acceptor sequence (i.e. a pyrimidine-rich stretch, TTCTCCCTTTTCGTTCCT, followed by AG) and the presence of a stop rather than a basic residue in the appropriate position of the derived amino acid sequence.

bBMP-3 is therefore characterized by the DNA and amino acid sequence of Table I A and Table I B. The peptide sequence of this clone is 175 amino acids in

TABLE I. A.

```
        383              393              403            413(1)                 428
GAGGAGGAAG CGGTCTACGG GGGTCCTTCT GCCTCTGCAG AAC AAT GAG CTT CCT GGG GCA
                                                Asn Asn Glu Leu Pro Gly Ala 443                       458                      473                     488
GAA TAT CAG TAC AAG GAG GAT GAA GTA TGG GAG GAG AGG AAG CCT TAC AAG ACT
Glu Tyr Gln Tyr Lys Glu Asp Glu Val Trp Glu Glu Arg Lys Pro Tyr Lys Thr 503                      518                     533
CTT CAG ACT CAG CCC CCT GAT AAG AGT AAG AAC AAA AAG AAA CAG AGG AAG GGA
Leu Gln Thr Gln Pro Pro Asp Lys Ser Lys Asn Lys Lys Lys Gln Arg Lys Gly 548                      563                     578                      593
CCT CAG CAG AAG AGT CAG ACG CTC CAG TTT GAT GAA CAG ACC CTG AAG AAG GCA
Pro Gln Gln Lys Ser Gln Thr Leu Gln Phe Asp Glu Gln Thr Leu Lys Lys Ala 608                     623                     638
AGA AGA AAG CAA TGG ATT GAA CCC CGG AAT TGT GCC AGA CGG TAC CTT AAA GTG
Arg Arg Lys Gln Trp Ile Glu Pro Arg Asn Cys Ala Arg Arg Tyr Leu Lys Val 653                      668                     683                      698
GAC TTC GCA GAT ATT GGC TGG AGC GAA TGG ATT ATT TCC CCC AAG TCC TTC GAT
Asp Phe Ala Asp Ile Gly Trp Ser Glu Trp Ile Ile Ser Pro Lys Ser Phe Asp 713                      728                     743 (111)             756
GCC TAT TAC TGC TCC GGA GCG TGC CAG TTC CCC ATG CCA AAG GTAGCCATTG
Ala Tyr Tyr Cys Ser Gly Ala Cys Gln Phe Pro MET Pro Lys 766              776              786
TTTTTTGTCC TGTCCTTCCC ATTTCCATAG
```

The region of bP-819 which hybridizes to Probe #1 and #3 is localized and sequenced. The partial DNA and derived amino acid sequences of this region are shown in Table IIB. The amino acid sequences corresponding to length and is encoded by the DNA sequence from nucleotide #414 through nucleotide #746 of Table I A and nucleotide #305 through nucleotide #493 of Table I B.

TABLE I. B.

```
            284              294              304 (112)               319
CTAACCTGTG TTCTCCCTTT TCGTTCCTAG TCT TTG AAG CCA TCA AAT CAC GCT ACC
                                         Ser Leu Lys Pro Ser Asn His Ala Thr 334                      349                     364                      379
ATC CAG AGT ATA GTG AGA GCT GTG GGG GTC GTC CCT GGA ATC CCC GAG CCT TGC
Ile Gln Ser Ile Val Arg Ala Val Gly Val Val Pro Gly Ile Pro Glu Pro Cys 394                      409                     424                      439
TGT GTG CCA GAA AAG ATG TCC TCA CTC AGC ATC TTA TTC TTT GAT GAA AAC AAG
Cys Val Pro Glu Lys MET Ser Ser Leu Ser Ile Leu Phe Phe Asp Glu Asn Lys 454                      469                     484         (175)
AAT GTG GTA CTT AAA GTA TAT CCA AAC ATG ACA GTA GAG TCT TGT GCT TGC AGA
Asn Val Val Leu Lys Val Tyr Pro Asn MET Thr Val Glu Ser Cys Ala Cys Arg
```

TABLE I. B.-continued

```
     503         513         523         533
TAACCTGGTG AAGAACTCAT CTGGATGCTT AACTCAATCG
```

EXAMPLE V

Human BMP-3

The bovine and human BMP-3 genes are presumed to be significantly homologous, therefore a human genomic library is screened with two oligonucleotide probes synthesized with the bovine BMP-3 sequence above. The oligonucleotides are as follows

1: d(AATTCCGGGGTTCAATCCATTGCTTTCTTCTTGCCTTCTTCAGGGTCTCTGT)
2: d(TTCGCTCCAGCCAATATCTGCGAAGTCCACTTTAAGGTACCGTCTGGCAC)

The oligonucleotides are synthesized on an automated synthesizer and radioactively labeled with polynucleotide kinase and $^{32}$p-ATP. A human genomic library (Toole et al., supra) is plated. Duplicate nitrocellulose filter replicas of the library corresponding to 1,000,000 recombinants are made of and hybridized to the nick-translated probes in 5×SSC, 5×Denhardt's, 100 ug/ml denatured salmon sperm DNA, 0.1% SDS (the standard hybridization solution) at 50 degrees centigrade for approximately 14 hours. The filters are then washed in 1×SSC, 0.1% SDS at 50 degrees centrigrade and subjected to autoradiography. Ten duplicate positives are isolated and plaque purified Sequence analysis indicates that the positives contain the human BMP-3 gene.

A region comprised of the bovine DNA sequence residues 408-727 in Table I.A. is subcloned into the plasmid pSP65 [see D. A. Melton et al., *Nucl. Acid Res.*, 12:7035-7056 (1984)], and amplified by standard techniques. The insert region of this plasmid is then excised and labeled with $^{32}$p by nick-translation. A primer-extended cDNA library is made from the human lung small cell carcinoma cell line H128 (ATCC#HTB 120) using as a primer an oligonucleotide of the sequence d(AATGATTGAATTAAGCAATTC). This oligonucleotide was synthesized on the basis of the DNA sequence of the 3' untranslated region of the human BMP-3 gene. 375,000 recombinants from this library are screened with the nick-translated probe by standard methods Recombinants from the library are hybridized to the probe in standard hybridization solution at 65 and washed in 0.2×SSc, 0.1% SDS at 65 degrees centigrade. 17 positives are obtained. One of these, λH128-4 was deposited with the ATCC on Mar. 31, 1988 under accession number 40437. The entire nucleotide sequence and derived amino acid sequence of the insert of H128-4 are given in Table II. This clone is expected to contain all of the nucleotide sequence necessary to encode the entire BMP-3 protein. The amino acid sequence of Table II is contemplated to represent a primary translation product which may be cleaved to produce the mature protein. The BMP-3 protein encoded by Table II is contemplated to contain the 96 amino acid sequence from amino acid #377 to amino acid #472 or a sequence substantially homologous thereto. The sequences corresponding to tryptic Fragments 9-12 are underlined in Table II. The DNA sequence indicates that the human BMP-3 precursor protein is 472 amino acids. It is contemplated that BMP-3 corresponds to the approximately 16 to 18 kd subunit of Example IIC.

The sequences of BMP-3 as shown in Tables I A and I B and II, have significant homology to the beta (B) and beta (A) subunits of the inhibins. The inhibins are a family of hormones which are presently being investigated for use in contraception. See, A. J. Mason et al, *Nature*, 318:659-663 (1985). To a lesser extent they are also homologous to Mullerian inhibiting substance (MIS), a testicular glycoprotein that causes regression of the Mullerian duct during development of the male embryo and transforming growth factor-beta (TGF-b) which can inhibit or stimulate growth of cells or cause them to differentiate. BMP-3 also demonstrates sequence similarity with Vgl. Vgl mRNA has been localized to the vegetal hemisphere of xenopus oocytes. During early development it is distributed throughout the endoderm, but the mRNA is not detectable after blastula formation has occurred. The Vgl protein may be the signal used by the endoderm cells to commit ectodermal cells to become the embryonic mesoderm

TABLE II

```
          10         20         30         40         50         60         70
AGATCTTGAA AACACCCGGG CCACACACGC CGCGACCTAC AGCTCTTTCT CAGCGTTGGA GTGGAGACGG 80         90        100        110        120        130        140
CGCCCGCAGC GCCCTGCGCG GGTGAGGTCC GCGCAGCTGC TGGGGAAGAG CCCACCTGTC AGGCTGCGCT 150        160        170        180        190        200        210
GGGTCAGCGC AGCAAGTGGG GCTGGCCGCT ATCTCGCTGC ACCCGGCCGC GTCCCGGGCT CCGTGCGCCC 220        230        240        250        260        270        280
TCGCCCCAGC TGGTTTGGAG TTCAACCCTC GGCTCCGCCG CCGGCTCCTT GCGCCTTCGG AGTGTCCCGC 290        300        310        320 (1)                335
AGCGACGCCG GGAGCCGACG CGCCGCGCGG GTACCTAGCC ATG GCT GGG GCG AGC AGG CTG CTC
                                              MET Ala Gly Ala Ser Arg Leu Leu 350             365              380              395
TTT CTG TGG CTG GGC TGC TTC TGC GTG AGC CTG GCG CAG GGA GAG AGA CCG AAG CCA
Phe Leu Trp Leu Gly Cys Phe Cys Val Ser Leu Ala Gln Gly Glu Arg Pro Lys Pro 410             425              440              455
CCT TTC CCG GAG CTC CGC AAA GCT GTG CCA GGT GAC CGC ACG GCA GGT GGT GGC CCG
Pro Phe Pro Glu Leu Arg Lys Ala Val Pro Gly Asp Arg Thr Ala Gly Gly Gly Pro
```

TABLE II-continued

```
             470               485               500               515
GAC TCC GAG CTG CAG CCG CAA GAC AAG GTC TCT GAA CAC ATG CTG CGG CTC TAT GAC
Asp Ser Glu Leu Gln Pro Gln Asp Lys Val Ser Glu His MET Leu Arg Leu Tyr Asp 530               545               560
AGG TAC AGC ACG GTC CAG GCG GCC CGG ACA CCG GGC TCC CTG GAG GGA GGC TCG CAG
Arg Tyr Ser Thr Val Gln Ala Ala Arg Thr Pro Gly Ser Leu Glu Gly Gly Ser Gln 575               590               605               620
CCC TGG CGC CCT CGG CTC CTG CGC GAA GGC AAC ACG GTT CGC AGC TTT CGG GCG GCA
Pro Trp Arg Pro Arg Leu Leu Arg Glu Gly Asn Thr Val Arg Ser Phe Arg Ala Ala 635               650               665               680
GCA GCA GAA ACT CTT GAA AGA AAA GGA CTG TAT ATC TTC AAT CTG ACA TCG CTA ACC
Ala Ala Glu Thr Leu Glu Arg Lys Gly Leu Tyr Ile Phe Asn Leu Thr Ser Leu Thr 695               710               725               740
AAG TCT GAA AAC ATT TTG TCT GCC ACA CTG TAT TTC TGT ATT GGA GAG CTA GGA AAC
Lys Ser Glu Asn Ile Leu Ser Ala Thr Leu Tyr Phe Cys Ile Gly Glu Leu Gly Asn 755               770               785               800
ATC AGC CTG AGT TGT CCA GTG TCT GGA GGA TGC TCC CAT CAT GCT CAG AGG AAA CAC
Ile Ser Leu Ser Cys Pro Val Ser Gly Gly Cys Ser His His Ala Gln Arg Lys His 815               830               845
ATT CAG ATT GAT CTT TCT GCA TGG ACC CTC AAA TTC AGC AGA AAC CAA AGT CAA CTC
Ile Gln Ile Asp Leu Ser Ala Trp Thr Leu Lys Phe Ser Arg Asn Gln Ser Gln Leu 860               875               890               905
CTT GGC CAT CTG TCA GTG GAT ATG GCC AAA TCT CAT CGA GAT ATT ATG TCC TGG CTG
Leu Gly His Leu Ser Val Asp MET Ala Lys Ser His Arg Asp Ile MET Ser Trp Leu 920               935               950               965
TCT AAA GAT ATC ACT CAA TTC TTG AGG AAG GCC AAA GAA AAT GAA GAG TTC CTC ATA
Ser Lys Asp Ile Thr Gln Phe Leu Arg Lys Ala Lys Glu Asn Glu Glu Phe Leu Ile 980               995               1010              1025
GGA TTT AAC ATT ACG TCC AAG GGA CGC CAG CTG CCA AAG AGG AGG TTA CCT TTT CCA
Gly Phe Asn Ile Thr Ser Lys Gly Arg Gln Leu Pro Lys Arg Arg Leu Pro Phe Pro 1040              1055              1070              1085
GAG CCT TAT ATC TTG GTA TAT GCC AAT GAT GCC GCC ATT TCT GAG CCA GAA AGT GTG
Glu Pro Tyr Ile Leu Val Tyr Ala Asn Asp Ala Ala Ile Ser Glu Pro Glu Ser Val 1100              1115              1130
GTA TCA AGC TTA CAG GGA CAC CGG AAT TTT CCC ACT GGA ACT GTT CCC AAA TGG GAT
Val Ser Ser Leu Gln Gly His Arg Asn Phe Pro Thr Gly Thr Val Pro Lys Trp Asp 1145              1160              1175              1190
AGC CAC ATC AGA GCT GCC CTT TCC ATT GAG CGG AGG AAG AAG CGC TCT ACT GGG GTC
Ser His Ile Arg Ala Ala Leu Ser Ile Glu Arg Arg Lys Lys Arg Ser Thr Gly Val 1205              1220              1235              1250
TTG CTG CCT CTG CAG AAC AAC GAG CTT CCT GGG GCA GAA TAC CAG TAT AAA AAG GAT
Leu Leu Pro Leu Gln Asn Asn Glu Leu Pro Gly Ala Glu Tyr Gln Tyr Lys Lys Asp 1265              1280              1295              1310
GAG GTG TGG GAG GAG AGA AAG CCT TAC AAG ACC CTT CAG GCT CAG GCC CCT GAA AAG
Glu Val Trp Glu Glu Arg Lys Pro Tyr Lys Thr Leu Gln Ala Gln Ala Pro Glu Lys 1325              1340              1355              1370
AGT AAG AAT AAA AAG AAA CAG AGA AAG GGG CCT CAT CGG AAG AGC CAG ACG CTC CAA
Ser Lys Asn Lys Lys Lys Gln Arg Lys Gly Pro His Arg Lys Ser Gln Thr Leu Gln 1385              1400              1415
TTT GAT GAG CAG ACC CTG AAA AAG GCA AGG AGA AAG CAG TGG ATT GAA CCT CGG AAT
Phe Asp Glu Gln Thr Leu Lys Lys Ala Arg Arg Lys Gln Trp Ile Glu Pro Arg Asn 1430              1445        (377)  1460              1475
 TGC GCC AGG AGA TAC CTC AAG GTA GAC TTT GCA GAT ATT GGC TGG AGT GAA TGG ATT
 Cys Ala Arg Arg Tyr Leu Lys Val Asp Phe Ala Asp Ile Gly Trp Ser Glu Trp Ile 1490              1505              1520              1535
ATC TCC CCC AAG TCC TTT GAT GCC TAT TAT TGC TCT GGA GCA TGC CAG  TTC CCC ATG
Ile Ser Pro Lys Ser Phe Asp Ala Tyr Tyr Cys Ser Gly Ala Cys Gln  Phe Pro MET 1550              1565              1580              1595
CCA AAG TCT TTG AAG CCA TCA AAT CAT GCT ACC ATC CAG AGT ATA GTG AGA  GCT GTG
Pro Lys Ser Leu Lys Pro Ser Asn His Ala Thr Ile Gln Ser Ile Val Arg  Ala Val
```

TABLE II-continued

```
          1610               1625               1640                1655
GGG GTC GTT CCT GGG ATT CCT GAG CCT TGC TGT GTA CCA GAA AAG ATG TCC TCA CTC
Gly Val Val Pro Gly Ile Pro Glu Pro Cys Cys Val Pro Glu Lys MET Ser Ser Leu 1670               1685                 1700
AGT ATT TTA TTC TTT GAT GAA AAT AAG AAT GTA GTG CTT AAA GTA TAC CCT AAC ATG
Ser Ile Leu Phe Phe Asp Glu Asn Lys Asn Val Val Leu Lys Val Tyr Pro Asn MET 1715        1730       (472)      1746        1756          1766        1776
ACA GTA GAG TCT TGC GCT TGC AGA TAACCTGGCA AAGAACTCAT TTGAATGCTT AATTCAATCT
Thr Val Glu Ser Cys Ala Cys Arg

1786
CTAGAGTCGA CGGAATTC
```

EXAMPLE

Expression of BMP-3

In order to produce bovine, human or other mammalian bone inductive factors, the DNA encoding it is transferred into an appropriate expression vector and introduced into mammalian cells or other preferred eukaryotic or prokaryotic hosts by conventional genetic engineering techniques. However the presently preferred expression system for biologically active recombinant human bone inductive factor is stably transformed mammalian cells.

One skilled in the art can construct mammalian expression vectors by employing the sequence of Tables I A and I B and II or other modified sequences and known vectors, such as PCD [Okayama et al., *Mol. Cell Biol.*, 2:161-170 (1982)] and pJL3, pJl4 [Gough et al., *EMBO J.*, 4:645-653 (1985)]. The transformation of these vectors into appropriate host cells can result in expression of a EMP-3 protein. One skilled in the art could manipulate the sequences of Tables I A and I B and II by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences there-form or altering nucleotides therein by other known techniques). The modified EMP-3 coding sequence could then be inserted into a known bacterial vector sequence procedures such as described in T. Taniguchi et al., *Proc. Natl Acad. Sci. USA*, 77:5230-5233 (1980). This exemplary bacterial vector could then be transformed into bacterial host cells and BMP-3 expressed thereby. For a strategy for producing extracellular expression of BMP-3 in bacterial cells., see, e.g. European patent application EPA 177,343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a BMP-3 protein factor of the invention from mammalian cells involves the construction of cells containing multiple copies of the heterologous BMP-3 gene. The heterologous gene can be linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.*, 159:601-629 (1982). This approach can be employed with a number of different cell types. For example, a plasmid containing a DNA sequence for a BMP-3 protein of the invention in operative association with other plasmid sequences enabling expression thereof and the DHFR expression plasmid pAdA26SV(A)3 [Kaufman and Sharp, *Mol. Cell. Biol.*, 2:1304 (1982)]can be co-introduced into DHFR-deficient CHO cells, DUKX-BII, by calcium phosphate coprecipitation and transfection, electroperation or protoplast fusion. DHFR expression transformants are selected for growth in alpha media with dialyzed fetal dalf serum, and subsequently selected for amplification by growth in increasing concentrations of MTX (sequential steps in 0.02, 0.2, 1.0 and 5 uM MTX) as described in Kaufman et al., *Mol Cell Biol.*, 5:1750 (1983). Transformants are cloned, and biologically active BMP-3 expression is monitored by rat bone formation assay described aobe in Example III. BMP-3 expression should increase with increasing levels of MTX resistance. Similar procedures can be followed to produce other BMP-3 family proteins.

As one specific example, to produced the BMP-3 protein of Example V, the insert of H128-4 is released from the vector arms by digestion with KpnI, blunting with T4 polymerase, ligating on an EcoRI adapter, followed by digestion with Sal I. The insert is subcloned into the EcoRI and Xho I cloning sites of the mammalian expression vector, pMT2CXM. Plasmid DNA from this subclone is transfected into COS cells by the DEAE-dextran procedure [Sompayrac and Danna PNAS 78:7575-7578 (1981); Luthman and Magnusson, Nucl.Acids Res. 11: 1295-1308 (1983)]and the cells are cultured. Serum-free 24 hr. conditioned medium is collected from the cells starting 40-70 hr. post-transfection.

The mammalian expression vector pMT2 CXM is a derivative of p91023 (b) (Wong et al., Science 228:810-815, 1985 ) differing from the latter in that it contains the ampicillin resistance gene in place of the tetracycline resistance gene and further contains a XhoI site for insertion of CDNA clones. The functional elements of pMT2 CXM have been described (Kaufman, R. J., 1985, Proc. Natl. Acad. Sci. USA 82:689-693) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in *E. coli*.

Plasmid pMT2 CXM is obtained by EcoRI digestion of pMT2-VWF, which has been deposited with the American Type Culture Collection (ATCC), Rockville, Md. (USA) under accession number ATCC 67122. EcoRI digestion excises the cDNA insert present in pMT2-VWF, yielding pMT2 in linear form which can be ligated and used to transform *E. coli* HB 101 or DH-5 to ampicillin resistance. Plasmid pMT2 DNA can be prepared by conventional methods. PMT2CXM is then constructed using loopout/in mutagenesis (Morinaga, et al., Biotechnology 84: 636 (1984). This removes bases 1075 to 1145 starting from thr Hind II site near the SV40 origin of replication and enhancer sequences of pMT2. In addition it inserts the following sequence:

5'PO—$_{813}$ CATGGGCAGCTOGAG-3' at nucleotide 1145. Plasmid pMT2 CXM DNA may be prepared by conventional methods.

EXAMPLE DVII

Biological Activity of Expressed BMP-3

To measure the biological activity of the expressed BMP-3 obtained in Example VI above, the EMP-3 is partially purified on a Heparin Sepharose column. 4 ml of the collected post transfection conditioned medium supernatant transfection supernatant from one 100 mm dish is concentrated approximately 10 fold by ultrafiltration on a YM 10 membrane and then dialyzed against 20 mM Tris, 0.15 M NaCl, pH 7.4 (starting buffer). This material is then applied to a 1.1 ml Heparin Sepharose column in starting buffer. Unbound proteins are removed by an 8 ml wash of starting buffer, and bound proteins, including BMP-3, are desorbed by a 3–4 ml wash of 20 mM Tris, 2.0 M NaCl, pH 7.4.

The proteins bound by the Heparin column are concentrated approximately 10-fold on a Centricon 10 and the salt reduced by diafiltration with 0.1% trifluoroacetic acid. Purified BMP-3 protein is approximately 95% substantially free from other proteinaceous materials. The appropriate amount of this solution is mixed with 20 mg of rat matrix and then assayed for in vivo bone and/or cartilage formation activity by the Rosen-modified Sampath - Reddi assay. A mock transfection supernatant fraction is used as a control.

The implants containing rat matrix to which specific amounts of human BMP-3 have been added are removed from rats after seven days and processed for histological evaluation. Representative sections from each implant are stained for the presence of new bone mineral with von Kossa and acid fuschin, and for the presence of cartilage-specific matrix formation using toluidine blue. The types of cells present within the section, as well as the extent to which these cells display phenotype are evaluated and scored as described in Example III.

Addition of human BMP-3 to the matrix material resulted in formation of cartilage-like nodules at 7 days post implantation. The chondroblast-type cells were recognizable by shape and expression of metachromatic matrix. The assay results indicate that approximately 200 ng of BMP-3 results in a score of at least +2. The amount of activity observed for human BMP-3 indicates that it may be dependent upon the amount of BMP-3 protein added to the matrix sample.

Similar levels of activity are seen in the Heparin Sepharose fractionated COS cell extracts. Partial purification is accomplished in a similar manner as described above except that 6 m urea is included in all the buffers.

The procedures described above the may be employed to isolate other related BMP-3 factors of insterest by utilizing the bovine BMP-3 or human BMP-3 factors as a probe source. Such other BMP3 protein may find similar utility in, inter alia, fracture repair, wound healing and tissue repair.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. An isolated DNA sequence encoding an osteoinductive protein said DNA sequence comprising a coding sequence selected from the group consisting of
   (a) nucleostide #414 through nucleotide #746 of FIG. IA and #305 through nucleotide #493 of FIG. IB.
   (b) nucleotide #321 through nucleotide #1736 of FIG. II,
   (c) naturally occurring allelic sequences and equivalent degenerative codon sequences of (a) and (b); and
   (d) sequences which
       (1) hybridize to any of sequences (a) and (b) or (c) under stringent hybridization conditions; and
       (2) encode a protein characterized by the ability to induce the formation of bone and/or cartilage.

2. An isolated DNA sequence encoding an osteoinductive protein said DNA sequence comprising nucleotide #414 through #746 of FIG. 1A and nucleotide #305 through #493 of FIG. 1B.

3. An isolated DNA sequence encoding an osteoinductive protein said DNA sequence comprising nucleotide #321 through #1736 of FIG. 2.

4. An isolated DNA sequence encoding an osteoinductive protein said DNA sequence comprising nudeotide #1 through #1794 of FIG. 2.

5. A vector comprising a DNA sequence of claim 1 in operative association with an expression control sequence for said DNA sequence.

6. A vector comprising a DNA sequence of claim 3 in operative association with an expression control sequence for said DNA sequence.

7. A vector comprising a DNA sequence of claim 4 in operative association with an expression control sequence for said DNA sequence.

8. A host cell transformed with the vector of claim 5 wherein said host cell is selected from the group consisting of mammalian, bacterial, yeast and insect cells.

9. A host cell transformed with the vector of claim 6.

10. A host cell transformed with the vector of claim 7.

11. The host cell of claim 9 wherein said host is mammalian.

12. The host cell of claim 10 wherein said host is mammalian.

13. A method of producing an osteoinductive protein, said method comprising the steps of (a) culturing in a suitable culture medium said transformed host cell of claim 8; and
(b) isolating and purifying said osteoinductive protein from said culture medium.

14. The method of claim 13 wherein said host cell is a mammalian cell.

15. A method for producing an osteoinductive protein comprising the steps of:
(a) culturing in a suitable culture medium a host cell transformed with the vector of claim 6; and
(b) isolating and purifying said osteoinductive protein from said culture medium.

16. A method for producing an osteoinductive protein comprising the step of:
(a) culturing in a suitable culture medium a host cell transformed with the vector of claim 7; and
(b) isolating and purifying said osteoinductive protein from said culture medium.

17. The method of claim 15 wherein said host cell is a mammalian cell.

18. The method of claim 16 wherein said host cell, is a mammalian cell.

* * * * *